United States Patent [19]

Zaiger et al.

[11] Patent Number: Plant 7,402

[45] Date of Patent: Dec. 25, 1990

[54] NECTARINE TREE "EARLIGLO"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of, Modesto, Calif. 95351

[21] Appl. No.: 456,847

[22] Filed: Dec. 18, 1989

[51] Int. Cl.[5] ..... A01H 5/00

[52] U.S. Cl. ..... Plt./41

[58] Field of Search ..... Plt. 41

*Primary Examiner*—James R. Feyrer

[57] ABSTRACT

A new and distinct variety of nectarine tree which has the following combination of unique desirable features.

1. Early maturity of fruit.
2. Low chilling requirement of approximately 200 hours.
3. Fruit with a high degree of red skin color.
4. Regular and heavy bearing of medium size fruit.
5. Fruit having firm flesh, good shipping and storage quality.
6. Fruit with good flavor and eating quality.

1 Drawing Sheet

ORIGIN OF THE VARIETY

The present variety of nectarine tree was originated by us in the experimental orchard located near Modesto, Calif. from a cross between a selected seedling with the identification number 37G870 and May Glo Nectarine (U.S. Plant Pat. No. 5,245). The female parent 37G870 originated as a peach from a cross of Ruby Gold Nectarine (U.S. Plant Pat. No. 3,101) and a low chilling peach of unknown parentage.

ASEXUAL REPRODUCTION OF THE VARIETY

Asexual reproduction of the new and distinct variety of nectarine tree was preformed by us in the experimental orchard located near Modesto, Calif. by budding and shows that all characteristics are established and transmitted through succeeding propagations and run true to the original tree in all respects.

SUMMARY OF THE NEW VARIETY

The new and distinct variety of nectarine tree is of large size, vigorous, upright growth and a regular and productive bearer of firm, yellow flesh, clingstone fruit having yellow skin, substantially overspread with an attractive red color. The fruit is further characterized by having good flavor and eating quality, being able to ship to long distance markets and being early in maturity, the maturity being 4 to 5 days before May Glo Nectarine (U.S. Plant Pat. No. 5,245).

PHOTOGRAPHS OF THE VARIETY

The accompanying color photographic reproductions show the foliage and fruit of the present new variety with the upper and lower surface of the leaves being illustrated, specimens of the fruit, an exterior and a sectional view of the fruit, with a fruit being divided on its suture plane to show flesh coloration and a stone remaining in place. The photographic illustration were taken shortly after being picked at maturity (firm ripe) and the colors are as nearly true as is reasonably possible in a color presentation of this type.

DESCRIPTION OF THE VARIETY

The botanical details of the present new and distinct variety of nectarine tree, its foliage, flowers and fruit are based on observations of specimens grown near Modesto, Calif., with color terminology (except those in common terms) referenced to Reinhold Color Atlas by A. Kornerup and J. H. Wanscher.

Tree:
- *Size.*—Large.
- *Vigor.*—Vigorous.
- *Form.*—Upright.
- *Density.*—Medium dense.
- *Production.*—Productive.
- *Bearer.*—Regular.

Trunk:
- *Size.*—Medium to large.
- *Texture.*—Rough to shaggy.
- *Color.*—Brown to grayish brown.

Branches:
- *Size.*—Medium.
- *Texture.*—Medium rough.
- *Lenticels.*—Medium size. Medium number.
- *Color.*—Grayish brown.

Leaves:
- *Size.*—Large. Average length — 5¾" to 6". Average width — 1½" to 1⅝".
- *Texture.*—Smooth.
- *Margin.*—Crenate.
- *Petiole.*—Medium length. Medium thickness.
- *Glands.*—Reniform. Medium size. Number varies from 1 to 4. Average number 2. Located on upper portion of petiole and base of leaf blade.
- *Color.*—Upper surface — green to dark green (28-E-7) to (28-F-7). Lower surface — green to grayish green (29-E-6) to (29-E-7).

Flower Buds:
- *Size.*—Medium to large.
- *Length.*—Medium

Flowers:
- *Size.*—Large — showy.
- *Pollen.*—Present.
- *Color.*—Pink.
- *Blooming period* Feb. 15, 1988 to Feb. 25, 1988. Varies slightly due to weather conditions.

Fruit:
- *Maturity when described.*—Firm ripe.
- *Date of first picking.*—May 20, 1988.
- *Date of last picking.*—May 25, 1988.

*Size.*—Medium. Average diameter axially — $2\frac{3}{8}''$. Average transversely in suture plane — $2\frac{3}{8}''$.

*Form.*—Globes — nearly symmetrical.

*Suture.*—Deep — extends from base to apex.

*Ventral surface.*—Usually lipped — some fruit lipped more on one side.

*Cavity.*—Elongated in suture plane. Average depth — $\frac{3}{8}''$ Average breadth — $\frac{3}{4}''$.

*Base.*—Retuse.

*Apex.*—Retuse. Usually depressed in suture plane.

Skin:

*Thickness.*—Medium.

*Texture.*—Tough, tenacious to flesh.

*Tendency to crack.*—None.

*Down.*—Wanting.

*Color.*—Yellow ground color (5-A-6) to (5-A-7). Overspread with red (10-B-8) to (10-C-8).

Flesh:

*Texture.*—Firm and meaty.

*Juice.*—Moderate.

*Ripens.*—Even.

*Flavor.*—Mild to sub-acid.

*Aroma.*—Slight.

*Fibers.*—Few, tender.

*Eating quality.*—Good.

*Color.*—Yellow to chrome yellow (4-A-7) to (5-A-7).

Stone:

*Type.*—Clingstone.

*Size.*—Large. Average length — $1\frac{1}{4}''$. Average breadth — $1''$. Average thickness — $\frac{5}{8}''$.

*Form.*—Ovid.

*Base.*—Round — some nearly straight.

*Sides.*—Mostly equal.

*Apex.*—Acuminate.

*Surface.*—Pitted throughout, heavier toward the base. Irregularly furrowed toward apex.

*Tendency to split.*—Very slight.

*Color.*—Light brown (6-B-5) to (6-C-5).

Use: Dessert Market — local and long distance.

Shipping quality: Good.

Storage quality: Good.

The new and distinct nectarine tree, its foliage and fruit herein described may vary in slight detail due to climatic, soil conditions and cultural practices under which the variety may be grown; the present description is that of the variety grown under the ecological conditions prevailing near Modesto, Calif.

We claim:

1. A new and distinct variety of nectarine tree, substantially as illustrated and described, characterized by its large size, vigorous, upright growth and a regular and productive bearer of medium size, firm, yellow flesh, early maturing, clingstone fruit, maturing 4 to 5 days before May Glo Nectarine (U.S. Plant Pat. No. 5,245); the tree is further characterized by having a low winter chilling requirement of approximately 200 hours and producing fruit with an attractive red skin color, good flavor and eating quality and the ability to store and ship to long distance markets.

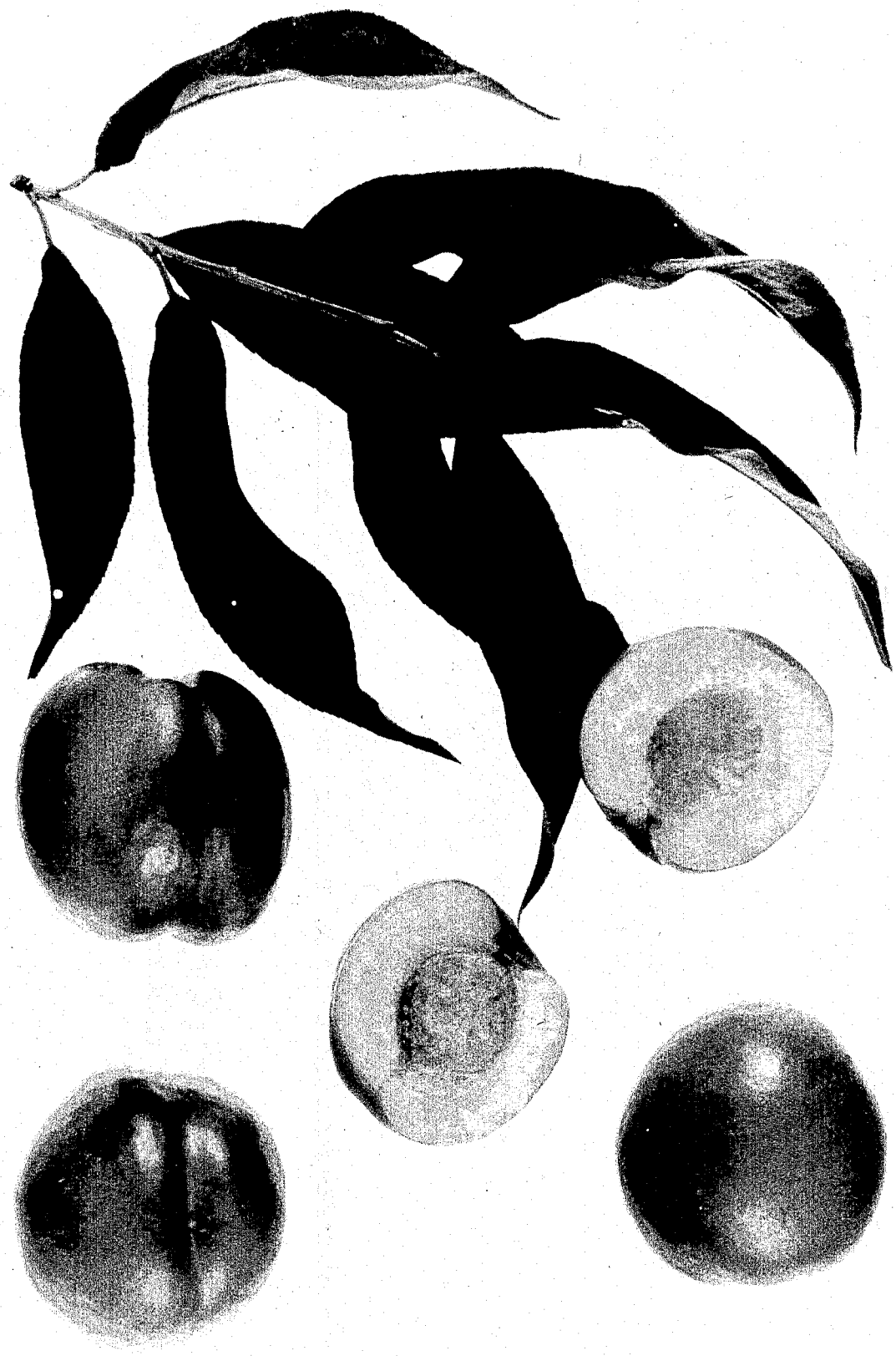

* * * * *